United States Patent
Tang

(10) Patent No.: US 8,092,842 B2
(45) Date of Patent: Jan. 10, 2012

(54) EXTRACTION OF PHYTOCHEMICALS BY ENZYMATIC HYDROLYSIS

(75) Inventor: Qingnong N. Tang, Saskatoon (CA)

(73) Assignee: Pos Pilot Plant Corporation, Saskatoon, Saskatchewan ( * ) Notice: Subject to any disclaimer, the term of this patent is extended or adjusted under 35 U.S.C. 154(b) by 196 days.

(21) Appl. No.: 12/525,277

(22) PCT Filed: Jan. 31, 2008

(86) PCT No.: PCT/CA2008/000217
§ 371 (c)(1),
(2), (4) Date: Sep. 1, 2009

(87) PCT Pub. No.: WO2008/092275
PCT Pub. Date: Aug. 7, 2008

(65) Prior Publication Data
US 2010/0021969 A1    Jan. 28, 2010

Related U.S. Application Data

(60) Provisional application No. 60/877,863, filed on Feb. 2, 2007.

(51) Int. Cl.
*A01N 65/00* (2009.01)
(52) U.S. Cl. ........................................................ 424/725
(58) Field of Classification Search .................. None
See application file for complete search history.

(56) References Cited

FOREIGN PATENT DOCUMENTS

| JP | 60-109526 | 6/1985 |
|---|---|---|
| JP | 61-289853 | 12/1986 |
| WO | WO 02/30219 | 4/2002 |
| WO | WO 2005/030235 | 4/2005 |

OTHER PUBLICATIONS

Predy, et al., "Efficacy of an extract of North American ginseng containing poly-furanosyl-pyranosyl-saccharides for preventing upper respiratory tract infections: a randomized controlled trial", Oct. 2005,. Can. Med. Assoc. J. 173(9):1043-1048.
Xue W., et al., "Application Study on Extraction and Separation Process of Effective Components from Medicinal Plants by Enzyme-membrane Method", Xibei Daxue Xuebao, Ziran Kexueban, Dec. 1997, vol. 27, No. 6, 99. 494-498, 1000-274X.
Guo, M., et al., "Extraction Study on Ginsenosides with Laccase", Shipin Kexue, 2006, vol. 27, No. 2, pp. 166-168, ISSN: 1002-6630.

*Primary Examiner* — Michael Meller
(74) *Attorney, Agent, or Firm* — Scott D. Rothenberger; Fulbright & Jaworski

(57) ABSTRACT

A process for extracting phytochemicals from plants. The process generally comprises controllably slurrying a selected plant material in a volume, adding a selected enzyme the slurry while it is controllably agitated, then heating the controllably agitated slurry-enzyme mixture to a temperature from the range of 40° C. to 110° C., and then maintaining the slurry-enzyme mixture at that temperature for a selected period of time. The slurry is then separated into a solids fraction and a liquids fraction that contains extracted phytochemicals. The liquids fraction is controllably de-watered to produce a fluid extract concentrate. The liquids fraction may optionally be dried to produce a dried extract concentrate. Suitable enzymes for use with this process include α-amylases, β-amylases, endo-β-1,4-glucanases, cellobiohydrolases, cellulases, hemicellulases, β-glucosidases, β-xylosidases, xylanases, pullulases, esterases and mixtures thereof.

6 Claims, 4 Drawing Sheets

EXTRACTION OF PHYTOCHEMICALS BY ENZYMATIC HYDROLYSIS

CROSS-REFERENCE TO RELATED APPLICATION(s)

This application is a Section 371 National Stage Application of International No. PCT/CA2008/000217, filed 31 Jan. 2008 and published as WO 2008/092278 A1 on 7 Aug. 2008, which claims priority from the U.S. Provisional Patent Application No. 60/877,863 filed Feb. 2, 2007, the contents of which are incorporated herein in their entirety for all purposes.

TECHNICAL FIELD

This invention relates to enzymatic hydrolysis processes for the extraction of phytochemicals. More particularly, the invention relates to processes for the extraction of polysaccharides, oligosaccharides and saponins from plant materials.

BACKGROUND ART

Traditionally, the roots of ginseng *Panax ginseng* C. A. Meyer commonly grown and available in Asia, are used clinically as a drug for anti-fatigue, anti-tumor, ant-cancer, stomachic disorders, immunological and energy booster, and stress relief in Oriental medicinal practices. It is known that the roots of *P. ginseng* contained several pharmacologically active saponins and polysaccharides. It is also known that *P. ginseng* extracts containing saponins and polysaccharides have immunostimulation and immunomodulation properties.

Ginseng fractions generated through chemical processes from North American ginseng *Panex quinquefolium* are known to have immunomodulatory effects. A recent randomized controlled study assessing the efficacy of North American ginseng *P. quinquefolium* extracts known to contain polyfuranosyl-pyranosyl-saccharides, for preventing upper respiratory tract infections was conducted by the University of Alberta with a total three hundred and twenty three subjects ranging between eighteen and sixty five years of age. The results showed that a standardized extract of North American ginseng *P. quinquefolium* was effective in reducing the absolute risk of recurrent colds and the mean number of colds per person (Predy et. al., 2005, Can. Med. Assoc. J. 173(9):1043-1048). Other studies with North American ginseng *P. quinquefolium* extracts produced by chemical processes showed these extracts enhanced test subjects' immune responses.

All the ginseng extracts available commercially and used in the previous studies were produced from chemical processes such as ethanol, methanol and aqueous extractions as well as chemical and chromatographic purifications. The chemical processes are complicated, costly and usually associated with low yields for the extracted saponins, oligosaccharides and polysaccharides.

DISCLOSURE OF THE INVENTION

The exemplary embodiments of the present invention are directed to processes comprising at least one enzyme hydrolysis step for the extraction of phytochemicals as exemplified by polysaccharides, oligosaccharides and saponins, from plant materials.

An exemplary embodiment of the present invention is directed to a process wherein a plant material is slurried in a volume of controllably agitated water producing a slurry. A catabolic enzyme is added to slurry for expressing an enzyme activity therein, after which the slurry is controllably heated to and maintained about a temperature selected from the range of 40° C. to 110° C. for a period of time selected from the range of 0.5 hour to 24 hours. A suitable temperature for thermo-stable α-amylase is 99° C.±6° C. A suitable time is about 3 hours. At the end of the selected period of time, the controllably agitated slurry is separated into a liquids fraction and a solids fraction. Water is controllably removed from the liquids fraction thereby producing an extract concentrate. The extract concentrate may be optionally controllably dried to produce a dry extract product.

According to one aspect, the plant material is selectable from a group comprising fresh whole plant parts, processed fresh plant parts, dried whole plant parts, and processed dried plant parts. Fresh whole plants may be suitably processed by maceration, pressing, chopping, shredding and grinding. Dried whole plants may be suitably processed by grinding, pulverizing, and chopping. A suitable plant material is a dried and powdered plant material.

According to another aspect, the catabolic enzyme is selected from the group comprising α-amylases, β-amylases, endo-β-1,4-glucanases, cellobiohydrolases, cellulases, hemicellulases, β-glucosidases, β-xylosidases, xylanases, pullulases, esterases and mixtures thereof. An exemplary suitable enzyme is α-amylase.

According to yet another aspect, the enzymatic activity is inactivated by heat or, in the case of thermo-stable α-amylase, by acidifying the controllably agitated slurry to a pH selected from the range of 2.0 to 3.75. A suitable acid for acidifying the slurry is exemplified by the group comprising citric acid, phosphoric acid and hydrochloric acid.

According to a further aspect, the solids fraction separated from said controllably agitated slurry is added to a second volume of water, controllably agitating the water thereby producing an agitated second slurry, controlling heating the agitated second slurring to a temperature selected from the range of 40° C. to 110° C., holding said controllably agitated second slurry at said selected temperature for a period of time selected from the range of 30 minutes to 24 hours, separating said controllably agitated second slurry into a second liquids fraction and a solids fraction, and combining said first liquid fraction and said second liquid fraction.

Another exemplary embodiment of the present invention is directed to a fluid extract concentrate prepared by a process wherein a plant material is slurried in a volume of controllably agitated water producing a slurry. A catabolic enzyme is added to slurry for expressing an enzyme activity therein, after which the slurry is controllably heated to and maintained about a temperature selected from the range of 40° C. to 110° C. for a period of time selected from the range of 0.5 hour to 24 hours. A suitable temperature for thermo-stable α-amylase is 99° C.±6° C. A suitable time is about 3 hours. At the end of the selected period of time, the controllably agitated slurry is separated into a liquids fraction and a solids fraction. Water is controllably removed from the liquids fraction thereby producing a fluid extract concentrate. The fluid extract concentrate may be optionally dried thereby producing a dried extract product.

BRIEF DESCRIPTION OF THE DRAWINGS

The present invention will be described in conjunction with reference to the following drawings, in which.

BEST MODES FOR CARRYING OUT THE INVENTION

Figure 1:
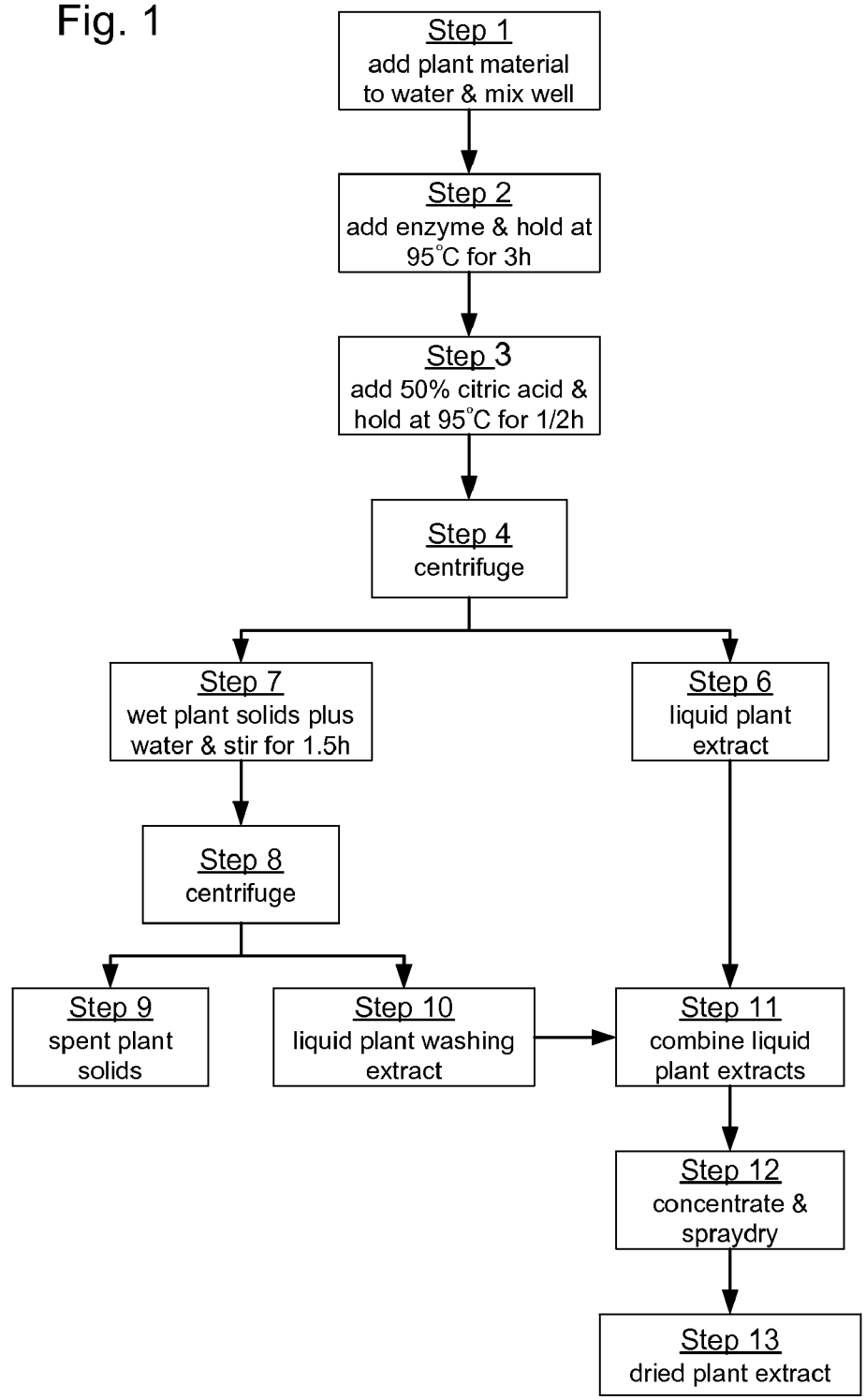
FIG. 1 is a schematic flow diagram illustrating a laboratory-scale process according to one embodiment of the present invention.
Figure 2:
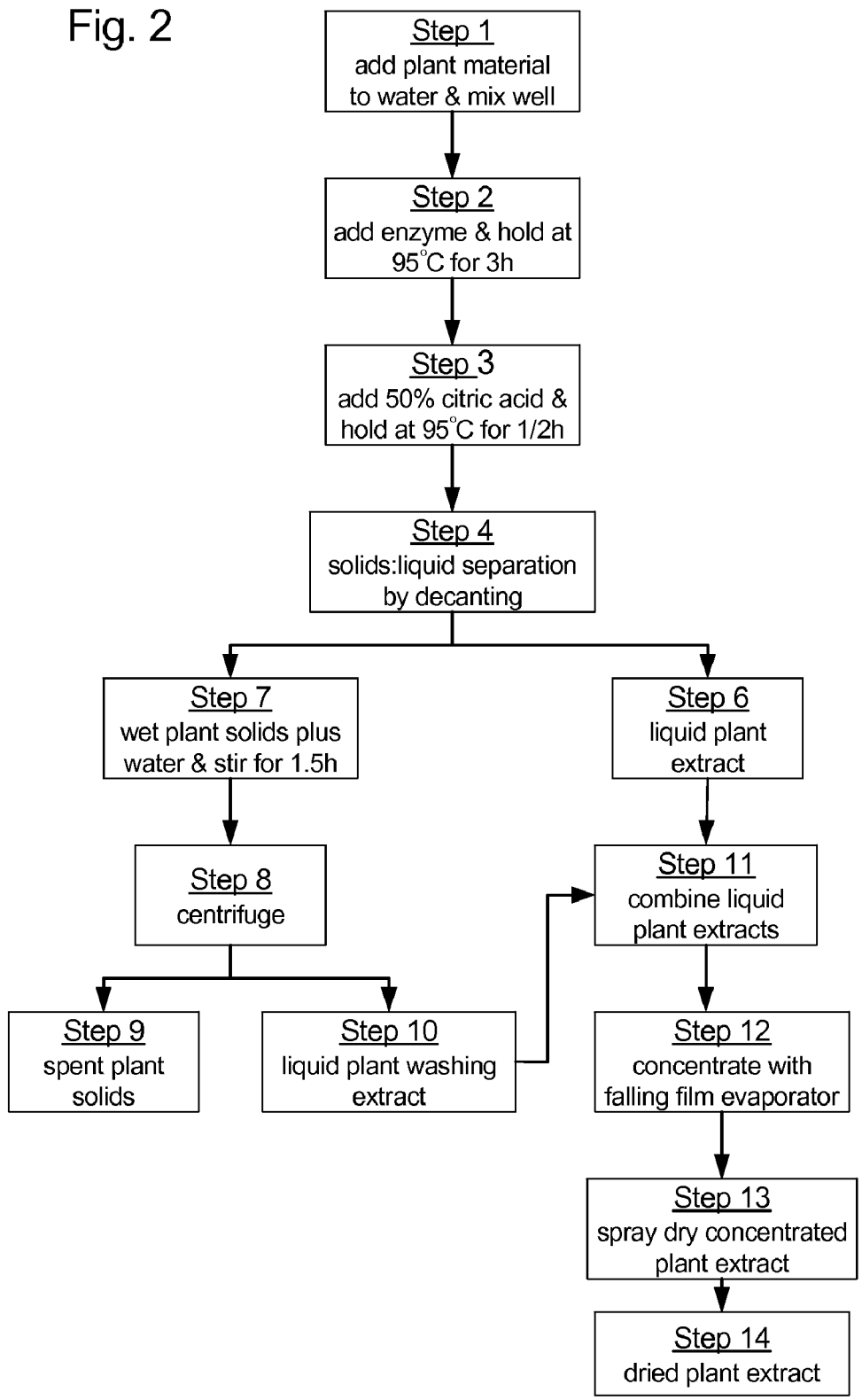
FIG. 2 is a schematic flow diagram illustrating a pilot-scale process according to a second embodiment of the present invention.
Figure 3:
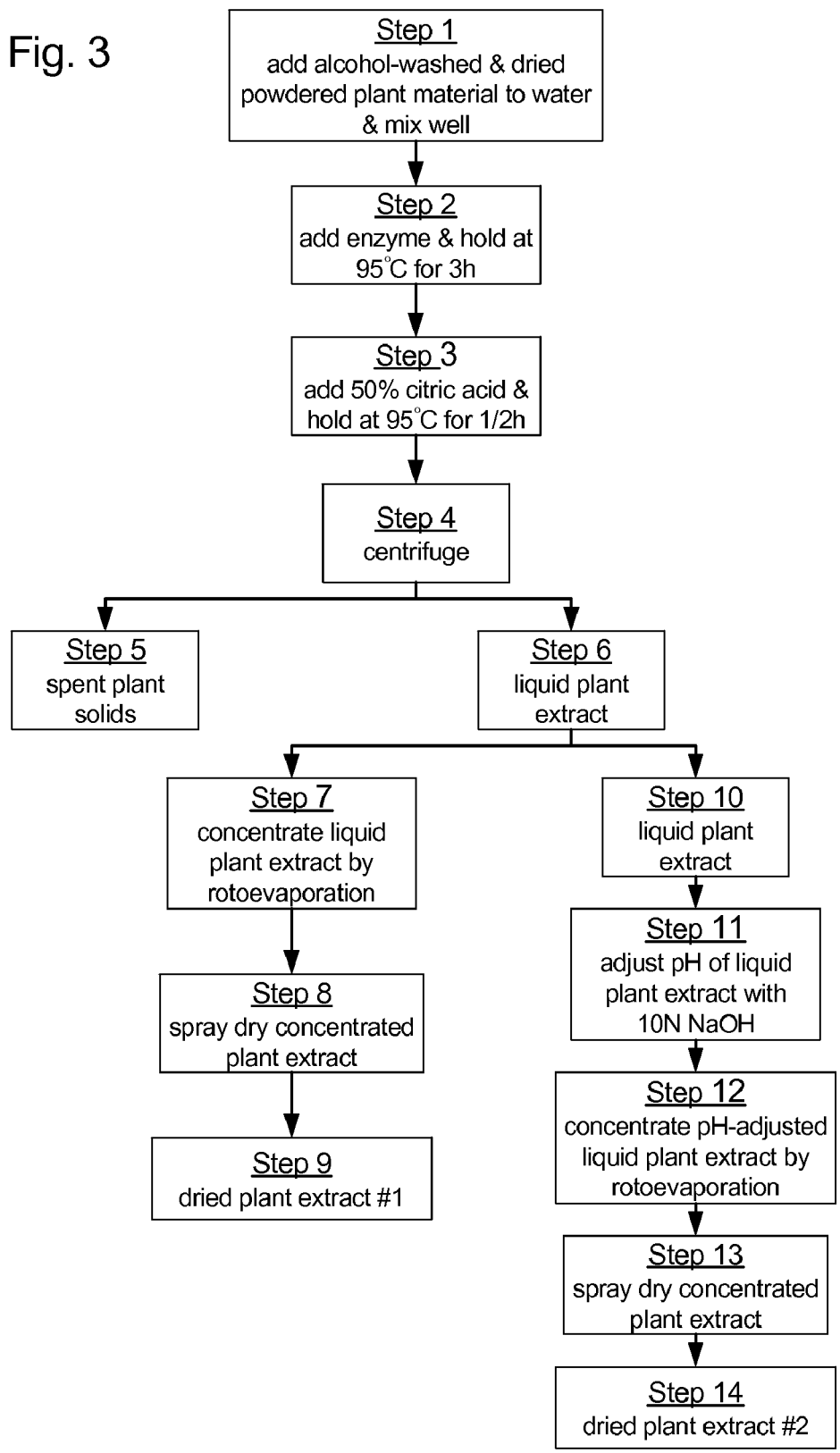
FIG. 3 is a schematic flow diagram illustrating a pilot-scale process according to another embodiment of the present invention.
Figure 4:
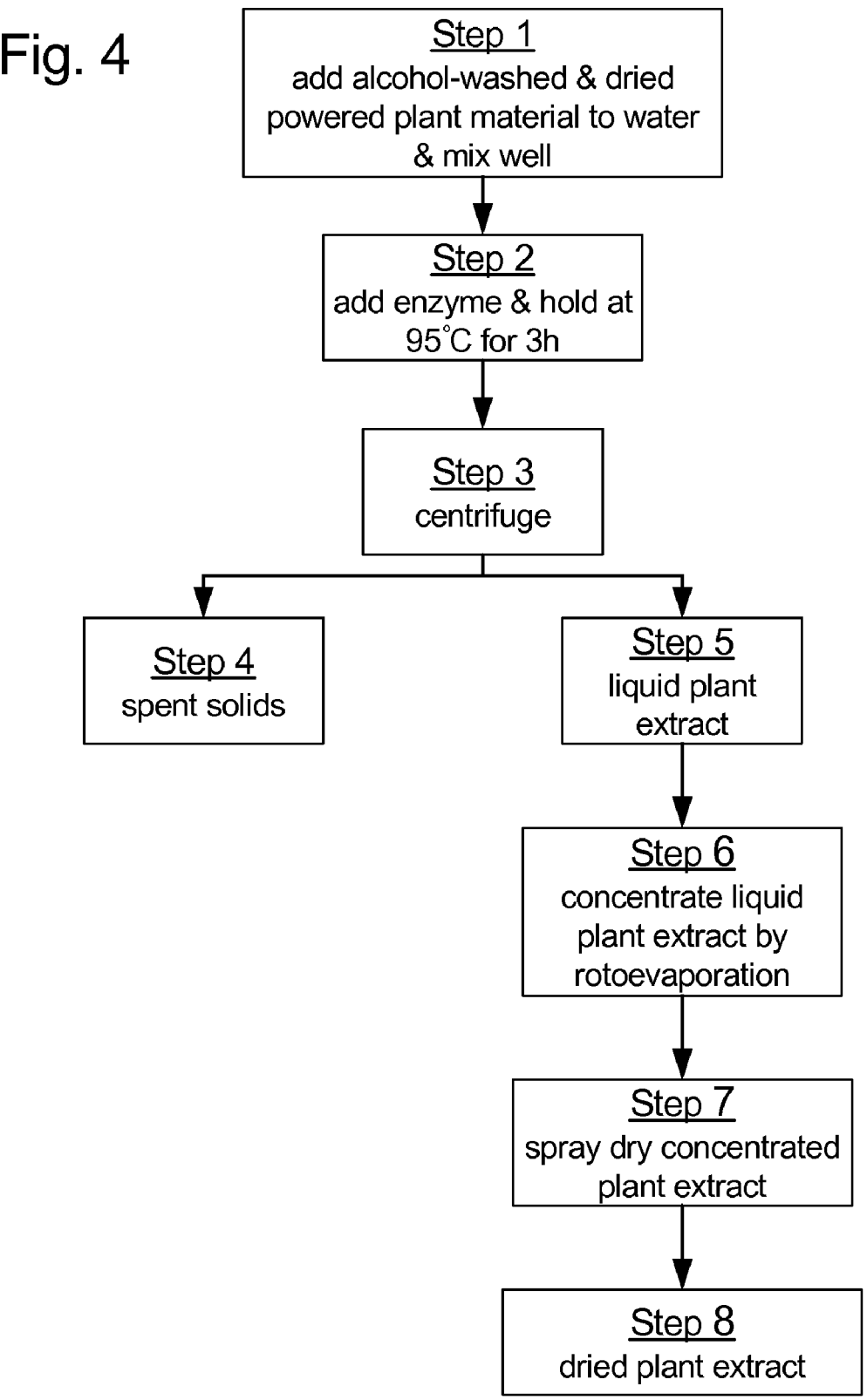
FIG. 4 is a schematic flow diagram illustrating a laboratory-scale process according to yet another embodiment of the present invention.

Exemplary embodiments of the present invention provide processes comprising enzyme hydrolysis for extraction of polysaccharides, oligosaccharides and saponins from powdered plant materials are shown in FIGS. 1-4. The first step generally comprises adding a plant material (PM) to water at a ratio from the range of 1:2 to 1:20 (PM:water) followed thorough mixing. Suitable plant materials for the processes of the present in invention include whole fresh plant parts, processed fresh plant parts, whole dried plant parts, and processed dried plant parts. An exemplary suitable plant material is a powdered dried plant material. The second step generally comprises adding an enzyme preparation to the PM:water mixture at a ratio from the range of 0.05% to 5% (enzyme:PM w/w) and heating the enzyme:PM:water mixture to about 40-110° C. and then holding the mixture at about 40-110° C. for about three hours under constant agitation. Suitable enzymes for the second step of the process are exemplified by α-amylases, β-amylases, endo-β-1,4-glucanases, cellobiohydrolases, cellulases, hemicellulases, β-glucosidases, β-xylosidases, xylanases, pullulases, esterases and mixtures thereof. It is within the scope of the present invention to provide an enzyme preparation comprising a single enzyme, or optionally, the enzyme preparation may comprise a plurality of compatible enzymes. Alternatively, the second step of the present may be adapted to provide a first substep wherein a first enzyme preparation is added to the PM:water mixture and maintained at an elevated temperature from the range of 40° C. to 110° C. for first enzyme reaction period after which, a second enzyme preparation is added to the PM:water mixture with is then maintained at the elevated temperature for a second incubation period. The third step generally comprises the inactivation of enzyme activity by heat or, in the case of thermo-stable α-amylase, by the addition of citric acid to the enzyme:PM:water mixture at a ratio from the range of 0.65% to 1.25% citric acid/enzyme:PM:water mixture, and the holding the mixture at about 95° C. for about thirty minutes. The fourth step generally comprises separating the inactivated PM:water mixture into a solids fraction and a first liquid fraction. The first liquid fraction is subsequently processed by evaporation to produce a dried product containing therein polysaccharides, oligosaccharides and saponins extracted from the powdered plant material. As shown in FIGS. 1 and 2, the solids fractions may be optionally further processed by washing with an additional volume of water, and then separation of the solids from the washing liquid to remove residual solubilized polysaccharides, oligosaccharides and saponins from the solids. The washing liquids may be combined with the first liquid fraction prior to the evaporation step to increase the recovery of polysaccharides, oligosaccharides and saponins extracted from the powdered plant materials. An optional first step as shown in FIG. 3 is to alcohol-wash and dry the powder plant materials prior to their addition into and mixing with water at a ratio selected from the range of 1:2 to 1:20. It is also within the scope of the present invention, as shown in FIG. 4, to omit the acidification and heat-kill step to inactive enzyme activity, but instead, to proceed directly to separation of the solids and liquid fractions.

The processes of the present invention are suitable for extraction of bioactive compounds from various types of tissues from various species of plants. For example, the processes disclosed herein can be adapted for:

(1) using one or more of α-amylase, cellulases and hemicellulases to extract bioactive compounds from *Echinacea angustifolia* roots. The *E. angustifolia* roots may be fresh macerated roots, or alternatively, dried powdered roots;

(2) using α-amylase to breakdown starch and purify proteins from corn gluten meal or corn starch and gluten slurry after degerminating and fiber removal in corn wet milling. The present processes may produce proteins that are over 95% pure for use as: (a) protein ingredients in foodstuffs, or (b) as the starting material for production of zein;

(3) using one or more of α-amylase, cellulases and hemicellulases to extract bioactive compounds from the roots of *Astralagus membranaceus*. The *A. membranaceus* may comprise fresh root materials or alternatively, dried root materials;

(4) using one or more of cellulases and hemicellulases to breakdown the cell walls of ginseng berries (e.g., *Panax ginseng* C. A. Meyer or *Panex quinquefolium*) to facilitate the extraction of triperpene saponins, oligosaccharides and polysaccharides; and (5) using α-amylase to extract saponins, oligosaccharides and polysaccharides from fresh or dried roots of *Panax ginseng* C. A. Meyer and *Panex quinquefolium*.

The examples presented below are included as exemplary embodiments of the present invention, but are not intended to limit the scope of the present invention.

EXAMPLE 1

A flow chart outlining one embodiment of the processes of the present invention is shown in FIG. 1 and exemplifies a two-step extraction of powdered ginseng roots at a laboratory scale. Dried North American ginseng root (*P. quinquefolium*) was supplied by Precise Hydroponics Inc., Edmonton, Alberta, Canada) and was milled into powder through a 24 mesh US screen. Approximately 300 g of the ground ginseng root were added to a mixing tank containing 3.6 kg of tap water under constant agitation (Step 1). The pH of the resulting slurry was determined to be 5.84. Approximately 1.5 g of α-amylase (e.g., Spezyme® Fred L supplied by Genencor International, Inc., Rochester, N.Y., U.S.A; Spezyme® is a registered trademark owned by Genencor International Inc.) was added to the ginseng slurry while constant agitation was maintained. The agitated slurry:enzyme mixture was heated to 95° C. and held at 95° C. for 3 hours to allow for the completion of starch hydrolysis (Step 2). The pH of the slurry dropped to 4.67 during the 3-hour hold at 95° C. Then, about 40 g of 50% citric acid was added to the slurry thereby reducing the pH further to 3.42. The acidified slurry was heated to and held at 95° C. for 0.5 hour in order to inactivate the α-amylase enzyme (Step 3).

After the α-amylase inactivation was completed, the ginseng slurry was separated by centrifugation at 4,414 g for 15 minutes into a first liquid fraction containing water-soluble extracts of polysaccharides, oligosaccharides and saponins, and a fraction comprising water-insoluble solids fraction (Step 4). The centrifugation step produced (a) about 1.45 kg of the first liquid fraction containing about 6.44% solids, and (b) about 1.49 kg of wet solids fraction containing about 13.13% solids. The 1.49-kg wet solids fraction was mixed with 1.5 kg of tap water and stirred for 1.5 hours to remove water-soluble polysaccharides, oligosaccharides and saponins from within the wet solids, and then centrifugated at 4,414 g for 15 minutes to separate the water-soluble extract washings from the spend solids. Approximately 1.75 kg of spend solids were obtained and disposed as waste. The water-soluble extract washings were combined with the first liquid fraction after which, the extracts in combined liquid fraction were concentrated by evaporation under reduced pressure at 80° C.±5° C. The concentrated extracts were then spray dried using conditions of 185° C.±5° C. inlet air temperature, 85° C.±5° C. outlet air temperature and 23° C. feed temperature resulting the production of about 122 g of dried extract having a moisture content of 4-8% moisture. The spray-died extract contained biologically active polysaccharides, oligosaccharides and saponins.

The process described here above was repeated for twice with different acids to determine if biological activities of the polysaccharides, oligosaccharides and saponins extracted from ginseng were affected by the type of acid used to inactivate the α-amylase enzyme at Step 3 (as shown in FIG. 1). In both follow-up studies, the pH of the enzyme:ginseng powder:water slurry was lowered to 3.5 while the temperature of the slurry was maintained at about 95° C. for 0.5 hour.

The effects of the ginseng extracts produced during these studies, on cell proliferation of lymphocytes isolated from Balb/C mice were assessed by the methods disclosed in Chapters 2 and 3 in Current Protocols in Immunology, (Coligan et al., Eds, 2007, John Wiley & Sons). A first positive control was lipopolysaccharide (LPS) at a concentration of 1 µg/ml. LPS (Prod. L4641) was supplied by Sigma-Aldrich Canada (Oakville, ON, Canada). A commercially available poly-furanosyl-pyranosyl-saccharide-rich ginseng extract, Cold-FX® (Cold-FX is a registered trademark of CV Technologies Inc., Edmonton, Alberta, Canada), was obtained from a local supermarket, and was used for comparison as a second positive control. The effects of the positive controls and the ginseng extracts produced by the three studies described herein on cell proliferation are shown in Table 1.

The amount of cell proliferation is related to the stimulation in the production of immunoglobulins. The ginseng extracts produced with the processes described in Example 1 stimulated the production of antibodies (i.e., immunoglobulins) when applied at concentrations of 10, 50 and 100 µg/ml. However, the data show that ginseng extracts produced by the processes using citric acid or hydrochloric acid to stop α-amylase activity produced more cell proliferation in this bioassay, than did ginseng extracts produced by the process phosphoric acid to stop α-amylase activity

TABLE 1

Effect of ginseng extracts produced with laboratory-scale processes comprising enzyme hydrolysis and different acids, on lymphocyte cell proliferation.

| Sample | Concentration (µg/ml) | Acid Used for Sample Preparation | Optical Density[a] |
|---|---|---|---|
| Negative control cells | n/a | — | 0.276 |
| Positive control #1 (LPS) | n/a | — | 0.361 |
| Positive control #2 (commercial ginseng extracts) | 10 | — | 0.322 |
| | 50 | — | 0.367 |
| | 100 | — | 0.299 |
| | 250 | — | 0.199 |
| Process 1 ginseng extracts | 10 | Citric Acid | 0.279 |
| | 50 | Citric Acid | 0.367 |

TABLE 1-continued

Effect of ginseng extracts produced with laboratory-scale processes comprising enzyme hydrolysis and different acids, on lymphocyte cell proliferation.

| Sample | Concentration (µg/ml) | Acid Used for Sample Preparation | Optical Density[a] |
|---|---|---|---|
| | 100 | Citric Acid | 0.367 |
| | 250 | Citric Acid | 0.392 |
| Process 2 ginseng extracts | 10 | Phosphoric Acid | 0.272 |
| | 50 | Phosphoric Acid | 0.291 |
| | 100 | Phosphoric Acid | 0.317 |
| | 250 | Phosphoric Acid | 0.303 |
| Process 3 ginseng extracts | 10 | Hydrochloric Acid | 0.305 |
| | 50 | Hydrochloric Acid | 0.393 |
| | 100 | Hydrochloric Acid | 0.342 |
| | 250 | Hydrochloric Acid | 0.284 |

EXAMPLE 2

The process described in Example 1 for testing in a laboratory scale was scaled to pilot-scale volumes as shown in FIG. 2. Dried North American ginseng root (*P. quinquefolium*) was obtained commercially and was milled into powder through a 24 mesh US screen.

Approximately 333.5 kg of ground ginseng roots were mixed with 4,669 kg of water under constant agitation in a 6,000 L stainless steel extraction tank. The ratio of water to the ground ginseng root was about 14 to 1 w/w. The ginseng slurry was heated to 97±2° C. under constant agitation, and its pH was determined to be 5.76. About 1.67 kg of α-amylase (Spezyme® Fred L supplied by Genencor International Inc.) was added to the slurry at a ratio of about 0.5% (enzyme: ginseng w/w). After addition of α-amylase enzyme, the ginseng slurry was heated to and held at 97° C.±2° C. for 3 hours under constant agitation to allow for sufficient time for starch hydrolysis. About 37.2 kg of citric acid were then added to the ginseng slurry to reduce the pH to about 3.28 after which the acidified slurry was heated to and held under constant agitation at 97° C.±2° C. for 0.5 hour for inactivation of the α-amylase enzyme. The acidified slurry was then centrifuged at 3,300 g centrifugal force using a Westfalia decanter (model CA225-010) to separate a first liquid fraction containing water-soluble extracts from the wet solids fraction. Approximately (a) 3,742 kg of a first liquid fraction containing 5.17% solids, and (b) 927 kg of a wet solids fraction containing 16.06% solids were produced.

The wet solids fraction (927 kg) were mixed with 1,670 kg of water under constant agitation in a stainless steel mixing tank for 5 hours at temperatures above 65° C., after which the slurry was passed through a decanter centrifuge to separate the spent solids fraction from the water-soluble washings liquid fraction. The weight of the spent solids fraction was about 900 kg and contained about 14.67% solids. The spent solids were disposed as waste. The recovered liquid fraction weight about 1,670 kg and contained about 1.53% solids.

The recovered water-soluble fraction and the first liquid fraction were combined and then concentrated using a Falling Film Evaporator (Universal Process Equipment Inc., Robbinsville, N.J., USA) at 40° C.±15° C. to produce 1,277.8 kg of a concentrated ginseng extract containing 17.59% solids. The pH of the concentrated ginseng extract was determined to be 3.29, and was then adjusted to pH 4.6 using a 4% NaOH solution. The pH-adjusted extract was then spray dried to produce 187 kg of a dried ginseng extract having a final moisture content of 6.4%.

The bioactivity of the dried ginseng extract produced with the pilot scale process disclosed herein was assessed using the assay, related methods, positive and negative controls as described in Example 1. The effects of the ginseng extract produced by the pilot-scale process described herein are shown in Table 2.

TABLE 2

Effects of a ginseng extract produced with a pilot-scale process of the present invention, on lymphocyte cell proliferation.

| Sample | Concentration (µg/ml) | Acid Used for Sample Preparation | Optical Density[a] |
|---|---|---|---|
| Negative control cells | n/a | — | 0.276 |
| Positive control #1 (LPS) | n/a | — | 0.361 |
| Positive control #2 | 10 | — | 0.322 |
| (commercial ginseng extracts) | 50 | — | 0.367 |
|  | 100 | — | 0.299 |
|  | 250 | — | 0.199 |
| Pilot-scale ginseng extract | 10 | Citric Acid | 0.333 |
|  | 50 | Citric Acid | 0.355 |
|  | 100 | Citric Acid | 0.421 |
|  | 250 | Citric Acid | 0.352 |

The ginseng extracts produced by the pilot-scale process disclosed herein provided stimulation of antibody production similar or greater than that provided by the two positive control treatments. The greatest stimulation of antibody production was provided by the 100 µg/ml treatment of the ginseng extract produced by the pilot-scale process.

EXAMPLE 3

Two studies were conducted to assess the effects of incorporating an alcohol wash pretreatment of the starting powdered plant materials on the extraction of polysaccharides, oligosaccharides and saponins with the processes of the present invention. Approximately 1 kg of ground ginseng root (*P. quinquefolium*) with a moisture content of about 7.2%, was mixed with 8 liters of 85% (v/v) ethanol. The alcohol-ginseng slurry was heated to 73° C.±3° C. and held at about that temperature for 3 hours under constant agitation. The alcohol-ginseng slurry was then filtered under vacuum through Whatman#1 filter paper to separate the ethanol-soluble extract from the wet solids fraction. About 5.88 liters of ethanol extract (about 5.39% solids content) and 2.2 kg of wet solids (about 32% solids content) were collected. The ethanol extract was concentrated and dried under vacuum at 75° C. using a Rotavapor to produce about 0.26 kg of dried saponin extract. The wet solids fraction was dried in a forced air oven at 85° C. for 0.5 hour. Approximately 0.68 kg of alcohol-washed dried ginseng meal at 3.66% moisture was produced.

The alcohol-washed ginseng meal so produced was then processed at a laboratory scale in a first study following the process flow outlined in FIG. 3. About 306 g of alcohol-washed dried ginseng meal were added to a mixing tank containing 3.6 kg of tap water under constant agitation (Step 1). Approximately 1.5 g of α-amylase (e.g., Spezyme® Fred L supplied by Genencor International, Inc.) was added to the ginseng slurry while constant agitation was maintained after which, the pH of the slurry was determined to be 6.18. The constantly agitated slurry:enzyme mixture was heated to about 95° C. and held at that temperature for 2.5 hours to allow for the completion of starch hydrolysis (Step 2). The slurry:enzyme mixture was heated to about 80° C. after which the pH was adjusted to about 3.46 with 50% citric acid. The acidified slurry was heated to and held at 95° C. for 0.5 hour in order to inactivate the α-amylase enzyme (Step 3).

After the α-amylase inactivation was completed, the acidified ginseng slurry was separated by centrifugation at 4,200 g for 15 minutes into a spent solids waste fraction (815.24 g) containing 18.0% solids, and a liquid ginseng extract fraction (2,925.9 g) containing 5.74% solids. The liquid ginseng fraction was separated into a 1,464.1-g first fraction and a 1,458.9-g second fraction. The first fraction was concentrated by evaporation at about 75° C. under vacuum using a Rotavapor apparatus to produce a concentrated ginseng extract containing 33.7% solids, which was then spray dried to produce 76.7 g of a first dried ginseng extract. The second fraction was adjusted with 10N NaOH to a pH of 6.18 after which it was concentrated by evaporation at 75° C. under vacuum using a Rotavapor apparatus to produce a concentrated ginseng extract containing 28.4% solids. The concentrated pH-adjusted second fraction was then spray dried to produce 68.2 g of a first dried ginseng extract.

The alcohol-washed ginseng meal produced as described herein was further processed at a laboratory scale in a second study following the process flow outlined in FIG. 4. About 200 g of alcohol-washed dried ginseng meal were added to a mixing tank containing 3.4 kg of tap water under constant agitation (Step 1). Approximately 1.0 g of α-amylase (e.g., Spezyme® Fred L supplied by Genencor International, Inc.) was added to the ginseng slurry while constant agitation was maintained after which, the pH of the slurry was determined to be 6.2. The constantly agitated slurry:enzyme mixture was heated to about 95° C. and held at that temperature for 3 hours to allow for the completion of starch hydrolysis (Step 2).

In this study however, the acidification to inactive enzyme activity was omitted. Instead, the slurry:enzyme mixture was centrifuged directly after the 3-hour holding period at 95° C. was completed. The slurry:enzyme mixture was separated by centrifugation at 4,200 g for 15 minutes into a spent solids waste fraction (594.4 g) containing 14.9% solids, and a liquid ginseng extract fraction (2,000.2 g) containing 5.07% solids. The liquid ginseng fraction was concentrated by evaporation at about 85° C. under vacuum using a Rotavapor apparatus to produce a concentrated ginseng extract containing 33.7% solids, which was then spray dried to produce 76.7 g of a first dried ginseng extract. The second fraction was adjusted with 10N NaOH to a pH of 6.18 after which it was concentrated by evaporation at 75° C. under vacuum using a Rotavapor apparatus to produce 226.4 g of a concentrated ginseng extract containing 41.6% solids. The concentrated pH-adjusted second fraction was then spray dried to produce 86.6 g of dried ginseng extract.

The polysaccharide, oligosaccharide and saponin extraction efficiency of the two enzyme processed described in this example, were compared to a prior art public domain process, i.e., the "control" reference point conducted as follows. About 100 g of alcohol-washed dried ginseng meal produced as described herein, were added to a mixing tank containing 1.2 kg of tap water under constant agitation to produce a ginseng slurry which was then heated to and held at about 95° C. for 3 hours to allow for the completion of starch hydrolysis (Step 2). The ginseng slurry was then centrifuged at 4,200 g for 15 minutes into a spent solids waste fraction (360 g) containing 14.7% solids, and a liquid ginseng extract fraction (942 g) containing 4.6% solids. The liquid ginseng fraction was concentrated by evaporation at about 85° C. under vacuum using a Rotavapor apparatus to produce a concentrated ginseng extract containing 20.1% solids, which was then spray dried to produce 43.4 g of dried ginseng extract.

Table 3 shows that the enzyme hydrolysis step of the present invention increased substantially the yield of dried ginseng extract from alcohol-washed ginseng meal, particularly when the enzyme was inactivated by acidification followed by partially adjusting the pH of the liquid fraction prior to drying.

TABLE 3

Effects of enzyme hydrolysis and enzyme inactivation on yields of ginseng extracts from alcohol-washed & dried ginseng meal.

| Component | Control | Study 1 | Study 2 |
|---|---|---|---|
| Alcohol-washed & dried ginseng meal (g) | 100 | 306 | 200 |
| Weight of water (kg) | 1.2 | 3.6 | 2.4 |
| Enzyme treatment | No | Yes[1] | Yes[1] |
| Enzyme inactivation treatment | No | Yes[2] | No |
| Dried ginseng extract produced (g) | 43.4 | 144.9 | 86.6 |
| Extraction yield (%)[3] | 43.4 | 54.9 | 50.7 |

[1] added 0.5% α-amylase relative to ginseng meal weight (w/w)
[2] α-amylase inactivated by acidification to pH 3.46 with 50% citric acid
[3] dried extract produced relative to alcohol-washed dried ginseng meal The biological activity of the dried ginseng extracts produced from alcohol-washed dried ginseng meal during the first study of this example was assessed using the assay and methods described in Example 1, and the results compared to the positive control #2 described in Example 1. The results are shown in Table 4. The ginseng extract produced by the enzymatic hydrolysis disclosed in study 1 of this example showed high stimulation on lymphocyte proliferation. It had higher stimulation than a popular commercially available ginseng extract on lymphocyte proliferation at a dosage of 100 μg/ml, but lower stimulation than the commercial ginseng extract at a dosage of 500 μg/ml. Both the popular commercially available ginseng extract and the extract generated from enzymatic hydrolysis are considered to have excellent stimulation on lymphocyte proliferation.

TABLE 4

Effects on lymphocyte cell proliferation by a ginseng extract produced from alcohol-washed ginseng meal with an enzyme hydrolysis process of the present invention.

| Sample | Concentration (μg/ml) | Acid Used for Sample Preparation | Lymphocyte proliferation (% of control) |
|---|---|---|---|
| Positive control #2 (commercial ginseng extract) | 100 | none | 359 |
|  | 500 | none- | 942 |
| Dried ginseng extract produced in Study 1 | 100 | Citric acid | 582 |
|  | 500 | Citric acid | 795 |

Enzymatic hydrolysis processes are disclosed herein for the use of enzymes exemplified by α-amylases, β-amylases, endo-β-1,4-glucanases, cellobiohydrolases, cellulases, hemicellulases, β-glucosidases, β-xylosidases, xylanases, pullulases, esterases and mixtures thereof, for the extraction polysaccharides, oligosaccharides and saponins from plant materials. Suitable plant materials for the processes of the present invention include whole fresh plant parts, processed fresh plant parts, whole dried plant parts, and processed dried plant parts. Such plant materials may be suitably alcohol-washed and dried prior to extraction with the processes disclosed herein. An exemplary suitable plant material is a powdered dried plant material. The processes are adaptable within the scope of this invention, by the selection of amylase enzymes for the extraction of polysaccharides, oligosaccha-rides and saponins from Asian ginseng (i.e., *Panax ginseng* C. A. Meyer) and American ginseng (*Panax quinquefolium*). This was the 1$^{st}$ time that extracts of saponins, polysaccharides and oligosaccharides were produced from ginseng roots through enzymatic hydrolysis based on published literature and patent applications. These extracts are believed to be rich in poly-furanosyl-pyranosyl-saccharides. The extracts generated from enzymatic hydrolysis processes using α-amylase in both the lab trials and the production run showed excellent stimulation on antibody production when compared to positive controls such as lipopolysaccharide and a popular commercially available ginseng extract. These extracts generated from enzymatic processes have potential to modulate natural and acquired immune responses. Those skilled in these arts will understand that if so desired, the active ingredients comprising the extracts may be separated and purified using conventional fractionation or separation methods.

The benefits of enzymatic processes for the extraction of saponins, polysaccharides and oligosaccharides from ginseng root are: higher extraction yield, lower extraction and processing cost, and elimination of potential processing problems related to starch gelatinisation during processing as compared with traditional chemical processes. The enzymatic processes are very simple, straight forward, robust, and cost-effective as compared with traditional chemical processes while yielding extracts with equal or better pharmaceutical and therapeutical properties.

While this invention has been described with respect to the preferred embodiments, it is to be understood that various alterations and modifications can be made to the enzyme-hydrolysis-based processes of the invention described herein for extraction of polysaccharides, oligosaccharides and saponins from plant materials.

What is claimed is:

1. A process for extraction of polysaccharides, oligosaccharides and saponins from ginseng to form a ginseng extract concentrate, the process comprising:
    a first step of washing ginseng with an alcohol solution and drying it to form a dried ginseng;
    a second step of adding the dried ginseng to a volume of water and controllably agitating said volume of water thereby producing a controllably agitated slurry of said ginseng;
    a third step comprising adding amylase to said controllably agitated slurry, said amylase selected for catabolizing at least one of cellulosic materials and starch materials, controllably heating said controllably agitated slurry to a temperature selected from a range of 40° C. to 110° C., and holding said controllably agitated slurry at said selected temperature for a period of time selected from a range of 0.5 hour to 24 hours;
    a fourth step comprising separating said controllably agitated slurry into a first liquid fraction and a first solid fraction;
    a fifth step comprising adding the first solid fraction to a volume of water, controllably agitating the water thereby producing a controllably agitated second slurry, controllably heating the controllably agitated second slurry to a temperature selected from a range of 40° C. to 110° C., holding said controllably agitated second slurry at said selected temperature for a period of time selected from a range of 30 minutes to 24 hours;
    a sixth step of separating said controllably agitated second slurry into a second liquid fraction and a second solid fraction;

a seventh step comprising commingling said first liquid fraction and said second liquid fraction to form a first and second liquid fraction;

an eighth step comprising concentrating said first and second liquid fraction by controllably removing water therefrom, thereby producing a ginseng extract concentrate.

2. The process of claim 1, wherein the process comprises an additional step of controllably drying said ginseng extract concentrate thereby producing a dried ginseng extract concentrate.

3. The process of claim 1, wherein the amylase is α-amylase.

4. The process of claim 1, wherein between the third and fourth step, controllably acidifying the controllably agitated slurry containing said amylase to a pH selected from a range of 2.0 to 3.75.

5. The process of claim 1, wherein the dried ginseng in the first and second step is in powder form.

6. The process of claim 1, wherein the alcohol solution in the first step contains at least one $C_{1-3}$ alcohol.

* * * * *